United States Patent [19]
Udy

[11] Patent Number: 4,980,295
[45] Date of Patent: Dec. 25, 1990

[54] PROCESS FOR DETERMINATION OF FAT CONTENT

[76] Inventor: Doyle C. Udy, 1909 Kedron Ct., Ft. Collins, Colo. 80524

[21] Appl. No.: 277,357

[22] Filed: Nov. 29, 1988

[51] Int. Cl.$^5$ ............................................. C01N 21/00
[52] U.S. Cl. ............................. 436/21; 436/22; 436/23; 436/60; 436/71; 436/86; 436/164; 436/171; 260/412.2; 260/412.4
[58] Field of Search .................. 436/21, 22, 23, 60, 436/71, 86, 164, 171, 909; 422/73; 260/412.2, 412.4; 426/430, 460

[56] References Cited

U.S. PATENT DOCUMENTS

| | | | |
|---|---|---|---|
| 2,863,734 | 10/1950 | Schain | 23/231 |
| 3,062,623 | 11/1962 | Schain | 23/230 |
| 3,351,431 | 11/1967 | Berry | 23/231 |
| 3,746,511 | 7/1973 | Stookey | 23/231 |
| 3,960,493 | 6/1976 | Beitz | 23/230 |
| 4,384,206 | 5/1983 | Bjarno | 436/21 |
| 4,497,898 | 2/1985 | Anderson et al. | 436/23 |
| 4,560,568 | 12/1985 | Curiel | 426/429 |
| 4,591,385 | 5/1986 | Pearsall | 264/16 |
| 4,747,979 | 5/1988 | Gimber et al. | 426/430 |
| 4,859,371 | 8/1989 | Diosady et al. | 260/412.4 |
| 4,866,983 | 9/1989 | Vinegar et al. | 436/31 |

OTHER PUBLICATIONS

Schmid, Peter CA79(15):89146d, Extraction and Purification of Lipids, 1973 (Physiol. Chem. Phys., 5(2), 141-50).

Official Method of Analysis of the Association of Official Analytical Chemists ("AOAC") Protocol No. 24,006, 14th Ed., 1984.

Primary Examiner—Robert J. Warden
Assistant Examiner—David Redding
Attorney, Agent, or Firm—Dorr, Carson, Sloan & Peterson

[57] ABSTRACT

The fat content of food or non-food products can be quickly and accurately determined by processes which solublize the product's fat content in tetrachloroethylene. These processes generally involve extracting the fat from a product to be tested for fat content with tetrachloroethylene, dissolving the fat/tetrachloroethylene solution in a polar organic solvent such as acetic acid, treating the resulting solution with an aqueous surfactant such as Triton X-100® in order to transfer the solution's fat content to the aqueous surfactant and thereby inducing the formation of fat globules in a resulting suspension and then testing the resulting suspension for monochromatic light dispersion. The light dispersed at the maximum turbidity of the sample is compared to a standard curve plot produced by previous tests on tetrachloroethylene solutions of a pure fat taken from samples comparable to the product being tested. The testing of some products may also require that methanol also be employed in conjunction with the tetrachloroethylene fat solvent.

20 Claims, 1 Drawing Sheet

PROCESS FOR DETERMINATION OF FAT CONTENT

BACKGROUND OF THE INVENTION

1. Field of the Invention

This invention generally relates to empirical methods for determining the fat and/or oil content of various food or non-food products. More specifically the invention is concerned with procedures for determining the fat and/or oil content of various products based upon the turbidity, and hence the ability to disperse light, of fat-containing extracts of such products.

2. Description of the Prior Art

Many industries, for example those associated with food production, the production of non-food products from plant or animal sources and various segments of the petroleum industry have need of processes for determining the fat and/or oil content of various fat and-/or oil-containing materials. For example, in the food and feed industries it is important to be able to quickly and inexpensively determine the fat and/or oil content of various products because such determinations are used for such varied purposes as nutritional labelling, grading, processing and payment. Such determinations are especially important to the meat, dairy, oilseed and animal feed industries.

Many industries associated with fat and/or oil-containing containing products, and especially the food manufacturing industry, also have found that it is not practical, or necessary, to rely upon only those exhaustive, but highly accurate methods used to determine the ultimate chemical composition of a given product. In other words, in many instances it is not necessary to break down a product into its separate chemical constituents and/or to determine its true physical properties. This is fortunate because highly accurate chemical breakdown tests are often based upon the completion of an entire series of complex, costly, time-consuming and/or hazardous steps which usually require precise chemical techniques carried out by highly skilled personnel. Nonetheless, many well known and widely used analytical tests used in industry in general, and the food industry in particular, have all these characteristics.

For example, one of the most common, and most successful methods for making a quantitative analysis for fat content has been the Roese-Gottlieb method. It deserves some description here in order to elucidate the nature and extent of its complexities. In applying this procedure to say a milk sample, one begins by applying to a test sample of 10 grams of milk, 1.5 ml. of ammonium hydroxide. Thereafter, a total of 95 ml. of chemicals is added in six separate transfers, with mixing and shaking after each transfer. More specifically, these chemicals comprise, in all, 15 ml. of 95% alcohol, 40 ml. of diethyl ether, and 40 ml. of petroleum ether. They are introduced, in steps, as follows: (1) addition to the sample to be tested of three different ingredients; (2) vigorous shaking for thirty seconds; (3) addition of another ingredient; (4) another thirty second period of shaking; (5) lapse of enough time for the solution to separate sufficiently for the portion in the upper part of the container to become relatively clear; (6) careful drawing off of the heavier or unclear portion cf the solution from the bottom of the container; (7) extraction of the clear liquid remaining in the container; (8) addition of two more ingredients to the clear liquid; (9) another thirty second period of shaking; (10) addition of another ingredient; (11) another thirty second period of shaking; (12) addition of another ingredient; (13) another thirty second period of shaking; (14) allowing the solution to stand again until the top portion is practically clear; (15) drawing off a clear fat solution into a flask or other storage vessel (if the complete removal of all fat is required, still one more extraction is advisable, moreover the fat solvent that is drained off in the second or third extraction must, of course, be added to the portion saved from the first extraction); (16) evaporating the total amount of fat solvent removed during the preceding steps; (17) drying the residue of fat remaining after the evaporation and (18) weighing the fat. Note also that this procedure is for liquid milk; the complexities for testing solid foods such as cheese are even more extensive.

Attempts to avoid the complexities of such tests and the skills required to perform them have resulted in the development of other less complex chemical procedures. For example, one alternative chemical procedure requires fewer steps; but it requires the use of a potentially hazardous substance, sulfuric acid. Yet another alternative procedure eliminates the need for the use of sulfuric acid, but it is very time consuming. Fortunately, however, it has often been found quite acceptable in industries such as the food processing industry to sacrifice high accuracy with respect to determining the exact chemical identity of a given food's chemical constituents for improvements in speed, cost, simplicity, reproducibility of results, etc., through the use of certain alternative testing procedures.

Such alternative tests are, almost without exception, empirical in nature. That is to say that such empirical methods do not evaluate a true physical content or property of a given material. Rather, empirical tests are designed to elicit a behavior or response from a material by placing the material in, or subject it to, a highly prescribed set of conditions and then measuring the material's response to those conditions. However, such a response must be reproducible and must not be interfered with by other, extraneous, variations. It also must be measurable to a reliability which can be correlated to a required degree of accuracy with the intrinsic property whose measurement has been avoided.

With regard to the need for such empirical analytical procedures in the food industry, testing usually focuses on certain considerations and ignores others. Such testing also naturally divides itself into certain categories. For example, in testing many foods one can simply ignore the presence of water, minerals and trace nutrient adjuncts such as vitamins, in order to concentrate on those nutrients ingested primarily for the purposes of "fueling" human beings and/or animals. Such nutrients are generally thought of as being comprised of three groups: (1) proteins, composed of polypeptides which are in turn composed of polymers of one or more alpha-amino acids, (2) carbohydrates, distinct structures of carbon with hydrogen and oxygen in the ratio of two atoms to one, and (3) fats and oils, composed principally of carbon, hydrogen and oxygen (fats and oils may also contain small amounts of other elements). In any case, fats and/or oils serve as the basic fuel of humans and animals (in contrast to quick energy sources), and have the virtue of being retained as reserves in the form of emulsions in the body for future use. Humans and animals convert surpluses of protein and carbohydrate into fats for future use as fuels.

Fats and oils are often roughly distinguished from each other to a large degree by their being in, respectively, a solid or a liquid state. They are often thought of as the collection of all other nutrients beside strictly structured proteins, sugars, and starches. It should be noted here, however, that for many food technology purposes and for the purposes of this patent disclosure, the terms "fat(s)" and "oil(s)" can be thought of as being synonymous. Chemically, they cover a vast variety of structural types: esters, lipids, glycols, steroids, glycerides, etc., and herein lies the source of many difficulties encountered in finding suitable analytical methods for their assay. Considering their chemical as well as their physical differences, it is probably not unduly pessimistic to suggest that a single procedure capable of selectively isolating and measuring each characteristic of a fat or an oil is no where on the food technology horizon. It best then, the food processing industry has usually sought out only those subtractive methods which have an ability to group as wide a variety of fats and oils as possible. Specific means are then found to remove or to otherwise ignore the effects of extraneous materials.

Some food technologies have taken a very different tack and abandoned the idea of a single, all embracing test method, and recognize, realistically, that no food material contains every kind of fat. For example, it is hardly necessary to provide for the presence of palmitins in fish, cholesterol in olive oil, stearins in corn, etc. Furthermore, in many applications the identification of the chemical character of fat content simply is not necessary. As a case in point, the heat of combustion (common food calories) of all fats and oils can be taken as 9 calories per gram, whether in butter, corn, oleo, or ham. Any error is usually within the error introduced by water content variation from sample to sample. Thus, it would seem that a practical approach for what might be called "control" testing of foods could be made bu first ascertaining the foods to be assayed and therefore the fats to be encountered. Second, an empirical test method need only be comprehensive for these materials. Finally, means of removal of major interferences may be sought. However, such removal is only necessary if it causes confusion in a control test, and if, in the correlation of results leading to the test calibration, then otherwise cannot be discounted or otherwise allowed for with sufficient accuracy. To these ends, the food industry has developed a number of empirical tests to determine the fat (and/or oil) content of various food products.

For example, U.S. Pat. No. 2,863,734 (the 734 patent) teaches a method for determining fat content (especially in fluid dairy products) by use of a detergent composed of two surface active agents. One of the surface active agents is an alcoholic, non-ionic agent which is employed to destabilize a fat emulsion. The 734 patent postulants that this action follows from the non-ionic agent's ability to solubilize protein-lecithin coatings surrounding fat globules and thereby destroying their stability as dispersed elements in an oil/water emulsion. The second surface active agent is an anionic agent whose function is to solubilize the non-fat material associated with the fat. Various anionic agents (e.g., dioctyl sodium phosphate) can be employed for this purpose. Measured quantities of the detergent composition are then added to measured quantities of a liquid dairy product sample. The mixture is also warmed to induce separation of a fat layer in the flask. A fat immiscible liquid is then added to displace the layer of fat into a graduated neck of the flask in order to measure the volume of said fat layer.

U.S. Pat. No. 3,062,623 ("the 623 patent") teaches a method for determining fat content, particularly in the context of blood serum. The process closely resembles the technology previously discussed with respect to the 734 patent. It also should be noted in passing that the 623 patent refers to the composition in the 734 patent as "a high molecular weight organic surface active agent having detergent properties". In any event, the 623 patent teaches use of the same general anionic surface active agents as those discussed in the 734 patent. It also teaches the use of another agent, ethoxy triglycol, to render the anionic surface active agent miscible in an aqueous medium. The 623 patent also suggests use of various alcohols, including methyl alcohol, as ingredients of the non-ionic agent compositions.

U.S. Pat. No. 3,351,431 teaches a fat content determination based upon use of a solvent comprising acetone, petroleum ether, and n-butyl alcohol. Essentially the process involves extraction of the fat with the solvent, physical separation of the fatty extract from the raffinate, evaporation of the solvent and weighing of the remaining dried fat.

U.S. Pat. No. 3,746,511 teaches a turbidimetric method for determining milk fat content. It employs acetic acid in combination with a class of surfactants having the general formula of certain quaternary halide salts: dialkyl, dimethyl ammonium halide, with the alkyl groups being the same. The turbidimetric aspect of this invention is based upon the formation of a colloidal dispersion of the milk fat which has a linear response of light absorbance in the 1.5 to 7 percent milk fat content range.

U.S. Pat. No. 3,960,493 teaches a nephelometric procedure which involves adding two distinct reagent solutions to a milk sample to form, sequentially and respectively, colloid dispersions of protein and fat, while effecting solubilization of the other. Nephelometric readings are taken after the addition of: (1) a protein reagent solution which is anhydrous (e.g., acetic anhydride, para-toluene sulfonic acid and acetic acid) and (2) a fat reagent solution, such as water with a small amount of non-ionic surfactant, whose function is to precipitate fat colloids.

U.S. Pat. No. 4,497,898 teaches a method of determining the fat content of milk by a triple-beam spectrophotometer system wherein two of the beams measure transmittance of separate streams of a sample, i.e., a stream with a reagent for developing coloration intensity proportional to the protein level and a reference stream without the color developing agent. The third beam measures the intensity of a light source. Comparison of the relative transmittance of the two streams to the relative transmittance of beams passing through a baseline fluid such as water enables one to determine separately, but in the same fashion, the protein and the fat content of the sample.

It should also be noted that some prior art methods of determining fat content of a fat-containing sample also have employed tetrachloroethylene as a fat solvent. For example, the reference source: Official Methods of Analysis of the Association of Official Analytical Chemists ("AOAC"), protocol number 24.006 of the 14th Ed., 1984, teaches fat extraction from a meat sample by use of tetrachloroethylene as a fat solvent. In this particular process, the fat is extracted from the meat in the presence of a drying agent such as $CaSO_4$. Thereafter, the fat extract is filtered and the specific gravity of the extract is correlated to the known fat content of samples.

The empirical processes disclosed in many of the above noted references usually employ phenomena associated with phase separation in liquids and/or phenomena associated with light-scattering. A few words with respect to each may be of some use here. With respect to phase separations, it is believed that an electrical double layer exists at the interface between the two phases of a colloidal dispersion. When the electric potential is measured between the so-called Guoy section of this double layer and the bulk dispersing phase, it is known as the "zeta potential". Its value is generally regarded as a partial indication of the stability of a colloidal system. It is probably not necessary to delve deeply into fundamental light-scattering theory, since many good reviews on the subject, in the context of food technology, are available (e.g., see Light Scattering by Milk Globules, by Walstra, Netherlands Milk Dairy Journal (19:93 (1965)). Suffice it to say that under certain conditions, turbid suspensions obey the Beer-Lambert law as applied to colored solutions. The attenuation of the light beam is due to scattering of light out of the direction of the incident beam rather than by molecular absorption.

With respect to the teachings of this patent disclosure, it should also be noted that it is well known that optical dispersion of a colloidal suspension of oil in an immiscible medium at a given wavelength is a function of the fat content in the suspension and thus of the fat content of the original sample. It is also known that since a visible absorption spectrum of such a suspension shows no peaks, the particular wavelength employed is arbitrary and may be chosen as convenient. However, those skilled in this art will appreciate that in any scattering and/or absorptiometric system, precautions have to be taken to eliminate reflection of scattered light back into the optical system. In addition, the use of an interference filler will insure maximum adherence to the Beer-Lambert law. It will also be appreciated that in colloidal systems of the type found in this patent disclosure, agglomeration will occur when the zeta potential is zero. Certain surfactants also are known to have an effect upon the zeta potential under certain conditions. Those skilled in this art also will appreciate that in an acidic solution, anionic and non-ionic surfactants have greatly reduced surface active properties, while cationic surfactants retain these properties.

With respect to the empirical use of such colloidal suspensions in general analytical chemistry, as well as in the context of this patent disclosure, it should also be noted that it is always desirable to use a stable, reproducible suspension in any measurement operation. This is especially true in automated continuous flow analysis where the optical surfaces of the flow cell must be kept as clean as possible in order to eliminate baseline drift. This pertains particularly to analysis of milk fats, where an unstable suspension rapidly produces a large buildup of aggregated colloidal particles throughout the glass part of the manifold, including the flowcell. Since agglomeration of colloidal particles also materially influences optical absorbance, this situation is to be avoided as much as possible.

In any event, each of the above noted techniques for determining the fat content of foods has certain virtues and drawbacks. The drawbacks usually revolve around the chemical complexity of the test, the accuracy achieved, the character of the ingredients and equipment and the time and skills needed to carry out the technique within prescribed degrees of precision. Hence any test which makes improvements in any of these areas of concern would be most welcome; this is especially true in the food processing industry.

SUMMARY OF THE INVENTION

The present invention provides improved processes for analyzing fat and/or oil-containing products in general (e.g., petroleum and mineral oil products) and food and feed products (e.g., dairy products, meats, grains, oilseeds, feeds, legumes, etc.) in particular. For the purposes of this patent disclosure the terms "fat(s)" and "oil(s)" may be used interchangeably to designate any or all of these entities. Regardless of nomenclature, the herein disclosed processes allow fat-containing products to quickly tested, either singly or as mixtures, to determine their individual or overall fat and/or oil content. Hence the disclosed processes are of particular value in the context of nutritional labeling, grading, processing, and payment determination in the food and feed industries; they are particularly well suited for determining the fat content of meat products, dairy products, oilseeds, grains and feeds. The major virtues of the herein disclosed processes reside in the fact that, compared with prior art methods, they provide faster and simpler methods for determining a product's fat and/or oil content without the need for expensive equipment and/or highly skilled labor. The disclosed processes also have the added advantage of being free of hazardous test conditions. Coupled with all of these desirable attributes, the processes of this patent disclosure also give results which are comparable in accuracy to those achieved by far more expensive and/or time consuming methods of fat or oil analysis which are presently employed in the food processing industry.

With respect to the application of the processes of this patent disclosure to food products, it should be specifically noted that they can be applied to many foods in their original liquid or their original solid state (however, many solid products, e.g., oilseeds, may have to be ground or otherwise prepared prior to testing). Such foods and/or other food materials also may be tested in emulsified or in clear phases. Moreover, any given food product may be tested while mixed with those other food materials which are often employed or encountered in the context of food processing. Yet another advantage of these processes in the context of food processing is the fact that they are not inclined to interference from proteins which are often present in a given food product and which often cause problems in other testing procedures. The disclosed processes also have the advantage that the relative proportions of the food materials and the chemicals used to conduct the tests, e.g., tetrachloroethylene, methanol, isopropanol, water, acetic acid, etc., when compared to the requirements of kinds of tests, may vary over relatively wide ranges without greatly effecting the end results.

Central to all of the herein disclosed processes for making fat determinations is the use of tetrachloroethylene as the fundamental solvent for extraction of the fat and/or oil content of the material being tested. Perhaps it also should be noted at this point that the terms perchloroethylene, or its acronym, PC, or the abreviation "perchlor", also may be used interchangeably in place of the term tetrachloroethylene and/or its chemical designation $C_2Cl_4$. In any event, the use of tetrachloroethylene coupled with methanol, or in some cases only tetrachloroethylene, is fundamental to the operative success of the herein disclosed processes. That is to say tetrachloroethylene coupled with methanol is extremely effective in solubilizing those water insoluble fats and/or oils found in various food and non-food products to such a degree, and in such a manner, that the fat content of a sample can be made the subject of certain turbidimetric tests which can be accurately correlated with the fat content of the sample material being tested.

Again, in some cases hereinafter more fully discussed, e.g., the extraction of fats from all dairy products, it is essential that the tetrachloroethylene solvent be used in conjunction with methanol. It should also be noted in passing that the methanol may be "pure" methanol or a methanol commonly having minor amounts of water. Indeed water may itself be used with the extractive solvents of this patent disclosure. The tetrachloroethylene/methanol combination may be employed (but need not be employed) in testing meat products. Indeed, applicant has found that there is virtually no fat or oil component in most foods in general commercial use which cannot be extracted in a combination of tetrachloroethylene and methanol and then be made the subject of the herein disclosed fat determination processes. When so employed, methanol forms a separate liquid phase with the water present or later added. It should be noted, however, that all of the extracted fat or oil still remains in the high-density non-polar tetrachloroethylene phase. This fact helps provide for a good separation between these two liquid phases.

Tetrachloroethylene also possesses many desirable ancillary attributes. For example, its toxicity is virtually nil (only by asphyxiation over long exposure). Furthermore, it is neither flammable nor detonable, and it is not an irritant to skin, and only mildly to the eyes, in large amounts. It also is cheap and plentifully available.

The disclosed processes are essentially comprised of a set of chemical and physical procedures performed in certain serial stages hereinafter more fully described. The most fundamental version of these processes generally involve obtaining a dissolved fat/tetrachloroethylene phase from a product to be tested for its fat content, dissolving the fat/tetrachloroethylene phase in a polar solvent such as acetic acid and treating the resulting true solution with an aqueous surfactant such as for example, Triton X-100 ®, or mixtures of Triton X-100 ®, isopropanol and water, in order to transfer the fat content of the resulting solution to the aqueous surfactant and thereby promoting formation of colloidal fat globules suspended in a resulting aqueous surfactant/fat suspension. In most cases, the aqueous surfactant/fat suspension need not be further separated from the tetrachloroethylene or the polar solvent. Hence the resulting suspension will be comprised of fat suspended in a mixture which normally will be an aqueous surfactant, tetrachloroethylene and polar solvent solution.

Other polar organic solvents that can be used in lieu of acetic acid are propionic acid, butyric acid, ethanol, propanol, isopropanol, etc. In fact, most organic solvents that are miscible with the perchlor/fat extract could i.e. used.

Surfactants can be employed to induce the formation of such fat globules. Triton X-100 ® (manufactured by Rohm and Hass Company) is a particularly effective surfactant for carrying out the processes of this patent disclosure. Besides triton X-100 ®, there are many nonionic surfactants that could be used. Surfynol surfactants manufactured by Air Products and Chemicals, Inc., Allentown, PA 18105 is a typical example. That is to say it is particularly effective in promoting the formation of fat globules from the fat/tetrachloroethylene/polar organic solvent solution, essentially, Triton X-100 ® is a nonionic, water soluble octylphenoxypolyethoxyethanol containing an average of 10 moles of ethylene oxide. By way of further example, applicant also has found that surfactants of isopropanol, water and Triton X-100 ® are particularly effective as surfactants !or the herein disclosed processes. Surfactant mixtures comprised of equal volumes of water and isopropanol in conjunction with about 0.1% (by volume) of Triton X-100 ® make highly preferred surfactants. In practice, an aqueous isopropanol, Triton X-100 ® surfactant in the above concentration will act best when about 3.5 ml of it is mixed with 0.35 ml of an extract (e.g., an oil in perchlor), which is dissolved in about 5 ml of acetic acid. Applicant has found that the isopropanol ingredient is useful in the surfactant for several reasons. It reduces the polarity of the water solution; it improves the miscibility of the water with the perchlor and it allows a larger volume of the surfactant solution to be used, which, of course, improves the tolerance level or sensitivity of the method. It also serves to reduce the temperature effect on turbidity, which can be an important consideration. The isopropanol is not, however, a indispensible ingredient for the success of these processes.

Regardless of the exact chemical nature of the surfactant however, the formation of fat globules produced by its introduction is then observed for their ability to disperse monochromatic light. Measurement of the light dispersed at or near the maximum turbidity generally gives the best overall fat content correlations. The maximum in turbidity is produced as a result of two opposing processes. On one hand the formation of fat globules is induced by introduction of the surfactant; while on the other hand those fat globules which have formed have a tendency to coalesce. This maximum turbidity will generally be reached in less than one minute after introduction of the surfactant. The time needed is a function of the fat/PC concentration. The light dispersion comparisons can be carried out in several ways well known to the art, but are usually most conveniently carried out by use of a spectrophotometer in its absorbance mode. The resulting turbidity readings are then compared &:o a standard curve.

The most preferred standard curve to which the maximum light dispersion reading of the sample can be compared are those standard curves produced by previous tests on tetrachloroethylene solutions of pure fats, in different concentrations, taken from comparable products (e.g., butter fat compared to butter fat, oilseed oil compared to like oilseed oil, etc.). Other standard curves are of course possible but are somewhat less referred. The actual observation of the maximum turbidity is most preferably accomplished by various comparative means known to the art including digital comparison, graphical interpolation, etc. It should also be completely understood that any "interpolation" or other comparison can be made by digital equipment as well as by other equipment and methods known to the art. Those skilled in this art will however appreciate that the best results are obtained by digital comparison. Extrapolation is usually an unacceptable means of comparison. Thus for example, should the absolute result, the percent of light dispersion by the sample, lie outside the range of dispersions observed in a calibration of the reference standard curve, the sample must be discarded; and properly sized, new sample(s) taken for assay. In common practice, in order to bracket possible inherent experimental variations, three samples of slightly different size are usually taken; calculations are not performed until all three results are complete. One sample is, however, permissible; two, not, in order to avoid operator bias.

Those skilled in the art will also appreciate that test results may themselves be used to infer the fat content of the original product or they may be used as data in equations (such as one hereinafter given and explained) used to calculate the fat content of the original product. Such equations can of course be made the subject of calculations based on digital operations.

Again, the fat extractive action of the tetrachloroethylene can be enhanced in many cases by its combined use with methanol as the fat extracting solvent. In fact, the use of methanol may even be regarded as approaching being an essential component of the extract solvent. For example, a methanol and tetrachloroethylene system will be required to extract the fat content of all dairy products. Thus the herein disclosed processes include processes specifically contemplating extracting the fat or oil content of a dairy product by initially performing the fat extraction by use of a mixture of methanol and tetrachloroethylene. Such extractions are most conveniently done in conjunction with vigorous agitation of the sample. Water can then also be added for solid products, to separate the methanol and split the solvent into two phases. Thereafter the creation and determination of turbidity and its relationship to fat content of dairy products are carried by the subsequent steps noted in the above procedures. The weight of the food product to that of the solvent (tetrachloroethylene or tetrachloroethylene and methanol) can vary considerably from food type to food type, but will generally fall in the range of about 32 parts (e.g. by weight) solvent to about that certain amount of food product that will yield about 130 mg fat. This parameter will generally produce very convenient sample sizes and accurate overall results. For example, one particularly preferred process for testing for the fat content of dairy products employs about 32 parts (e.g., by weight) tetrachloroethylene, to about 5 parts of methanol (also by weight).

Non-homogeneous solid food products (e.g., meats, grains, oil seeds, etc.) usually must be chemically and mechanically prepared for solubilization of their fat content (e.g., by grinding, comminution, maceration, homogenizing, etc. before they are exposed to the solvent action of the tetrachloroethylene or tetrachloethylene and methanol. By use of tetrachloroethylene (perchlor) and an UDY Extract-R-Reactor, (Udy Corporation, Fort Collins, Colorado) fats or oils from most materials can be fully extracted within two minutes. An aliquot of the filtered extract is dissolved in acetic acid and then mixed with a surfactant. The peak absorbance of the resulting turbid suspension of fat globules is measured at 480 nm using a digital colorimeter. In some of the more preferred embodiments of these processes, meat products will be prepared for testing by maceration and reductior to an emulsion in water and/or methanol and water. In another preferred embodiment of this process, meats will be prepared by transforming them into a homogeneous liquid or cream like solution in an aqueous surfactant such as one prepared from methanol, citric acid and water.

Stated in more detailed process terms, some of the more preferred embodiments cf these processes may be illustrated, but should rot be limited by the following additional exemplary versions of the herein disclosed processes. For example, one more detailed version of the processes of this patent disclosure can be specifically directed at fat-containing liquid food products (e.g., milk); it will generally comprise: (1) mixing the liquid food product vigorously with tetrachloroethylene and methanol in order to dissolve the liquid food product's fat content into the tetrachloroethylene in order to form a fat extract/tetrachloroethylene phase and an aqueous methanol phase (wherein the water of the aqueous phase is supplied by the water of the liquid being tested, e.g., the water which constitutes most of the milk) which contains the remainder of the food product; (2) filtering the fat extract/ tetrachloroethylene phase, (3) removing a measured (preferably measured by volume, and especially an aliquot) portion of said fat extract/ tetrachloroethylene phase; (4) mixing the measured portion of the fat extract/tetrachloroethylene phase with a polar solvent such as acetic acid in order to further solubilize the fat content of the fat extract/tetrachloroethylene phase, (5) mixing the solubilized fat content of the measured portion with an aqueous surfactant, particularly an aqueous surfactant containing Triton X-100 ® (such, as for example, a mixture of aqueous isopropanol and Triton X-100 ® in order to transfer the fat content of the fat-containing measured portion to the aqueous surfactant (for example to transfer the fat to a mixture of aqueous isopropanol and Triton X-100 ®), and thereby form colloidal globules of the fat which are suspended in say, the resulting aqueous isopropanol/Triton X-100 ®/fat suspension sample; (6) observing the fat suspension sample for a maximum in its ability to disperse monochromatic light; and (7) comparing the observed maximum in the dispersion of monochromatic light of the sample with a reference curve produced by the maximum dispersion of light produced by analogous fat suspensions of different known concentrations whose fat components are taken from a comparable food product and subjected to the appropriate, analogous, steps of dissolution in the polar organic solvent, introduction of the aqueous surfactant and observation for maximum turbidity.

Another version of this process is specifically aimed at testing solid food products (e.g., oil-containing seeds); it comprises the additional steps of making the solid product susceptible to the fat extraction action. The most common procedures for producing such susceptibility are subjecting the solid product to grinding, attrition, crushing and the like. Thereafter the resulting solid particles may be exposed to water and/or methanol prior to the fat extractive action of the tetrachloroethylene or tetrachlorothylene/methanol solvent. It should also be noted that although the preparative mechanical steps for solids may be done in many ways known to the art, applicant has found that the exposure to the fat-extracting solvent is best carried out by a device employing a free moving metal pestle in a tube with closed ends. Such a tube contains the solvent and substance to be extracted in the manner generally taught by U.S. Pat. No. 3,010,666. The disclosed tube and its contents are clamped to a motorized device which rapidly oscillates the tube. This motion, in turn, causes the pestle to strike either end of the tube in rapid succession and produces a completely acceptable level of extraction within a minute or two.

Finally those skilled in the art will also appreciate that in some respects the processes of this patent disclosure should be more rigidly followed than others. For example, whatever were the smallest details of a given calibration procedure, these very same details should be meticulously followed for the unknown sample. This caveat applies not only for equipment and materials, but also for such parameters as ambient conditions, time durations, etc. In this regard, corrections for differences in temperature may be especially important. Needless to say, the sample also must be calibrated by the same kind of product and in the same form, size and combination. Finally, those skilled in this art will also appreciate that measured (e.g., aliquot) portions must be predetermined such that the results fall within the range of the reference curve.

DESCRIPTION OF THE PREFERRED EMBODIMENTS

Figure 1:
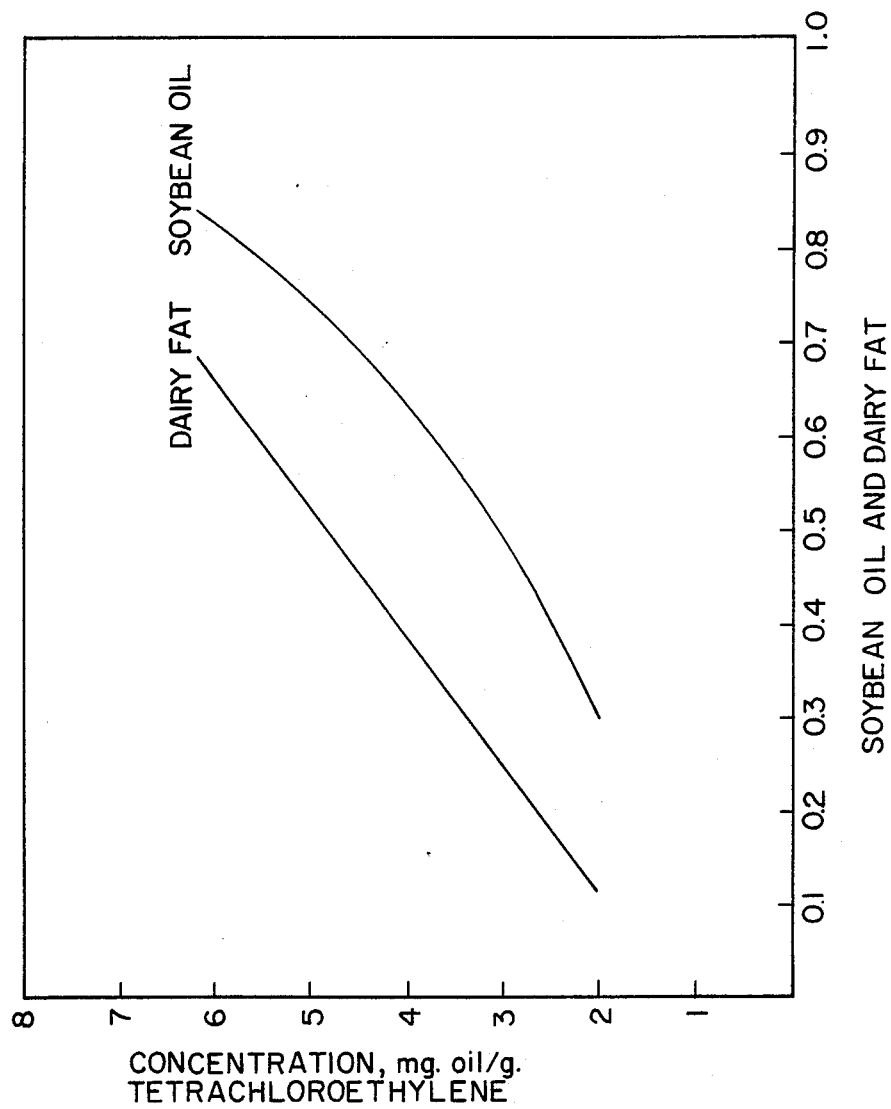
FIG. 1 depicts two typical standard curves (fat concentration, mg fat/g PC vs. absorbance) for a fat and/or an oil extracted from two representative food products (dairy fat and soybean oil) according to official standard reference methods promulgated by the AOAC. In each case, the saxles used to construct the standard curve are comprised of different concentrations of the subject fat or oil dissolved in tetrachloroethylene. Such solutions are then subject to dissolution in acetic acid, introduction of an aqueous surfactant and light dispersion tests according to the teachings of this patent disclosure.

The quantities of the sample products and chemicals employed to conduct the processes of this patent application may vary, but should produce results which fall in the range of the standard curve. Applicant has found that the best results are obtained when the quantities of each component are measured within about 0.5% of certain reference amounts for each ingredient. The sample size will of course serve to define the amount of the other chemicals which will be needed.

Sample size depends mostly on the expected fat content of the product. In order to obtain a fat in perchlor concentration within the 2.0 to 6.0 mg fat per gram of perchlor, the sample size is, of course, dependent upon the fat expected to be available in any given product. The volume or weight of perchlor is limited by the volume of the glassware selected (e.g., extract-R-tube). An optimum nominal volume of perchlor is 20 ml. This can vary by two or three ml either way. It is only necessary to know the weight of perchlor within about 30 mg in order to have an insignificant effect on the calculated result. For example, representative details of a typical test procedure might begin by first selecting a sample amount (e.g., about 0.650 grams in the case of say cheese, 0.800 grams in the case of meat, 0.750 grams in the case of soybeans) sufficient to give about 2.5 to about 4.5 mg of fat or oil per gram of tetrachloroethylene.

Some relative proportions, stated in ranges, for the perchlor ingredient, in a group of products to be tested might be as follows:

| Product | Expected % Fat | Sample Size | Perchlor |
|---|---|---|---|
| Pork | 20.0 | 0.290 to 1.050 grams | 29 to 35 grams |
| Bovine Milk | 3.50 | 1.66 to 6.00 grams | 29 to 35 grams |
| Soybean | 18.0 | 0.322 to 1.170 grams | 29 to 35 grams |
| Corn | 4 | 1.45 to 5.25 grams | 29 to 35 grams |
| Peanuts | 30 | 0.193 to 0.700 grams | 29 to 35 grams |

| Product | Acetic Acid | Triton X-100 ® |
|---|---|---|
| Beef | 4.9 to 5.1 grams | 3 to 4 mg. |
| Bovine Milk | 4.9 to 5.1 grams | 3 to 4 mg. |
| Soybean | 4.9 to 5.1 grams | 3 to 4 mg. |

Where applicable (e.g., in the case of solid samples) the sample must be initially prepared for fat extraction. Other samples (e.g., milk) will need no preparative steps. The sample can then be placed in from about 31 to about 33 grams of tetrachloroethylene and about 4.5 to 5.0 grams of methanol and the resulting mixture vigorously agitated. The fat extract/tetrachloroethylene sample (e.g., about 0.34 to about 0.36 mil) is then preferably dissolved in about 4.90 to about 5.10 ml of acetic acid. To the resulting solution is then added about 3.4 to about 3.6 ml of a surfactant comprised of approximately 1:1 isopropanol with aqueous 0.2% Triton X-100 ®. When the sample being tested is dry (e.g., less than about 20% water) about 4 to about 6 ml of methanol also can be added to the sample material and the tetrachloroethylene. In some cases water, e.g., about 6 ml of water, can be added to the system after the extraction step. On the other hand, when the sample has more than about 20% (by weight) water, it is not usually necessary to add any water to the system.

EXAMPLE I—RE: SOLID FOOD PRODUCTS

A portion of a low moisture, solid food product such as a grain, oilseeds, legume, or feed material is first prepared for testing by grinding it up, preferably to a particle size of about 0.5 mm and smaller. Blending with bentonite clay before grinding also may be useful for certain high fat or oil commodities, e.g., sunflower seed. If the substance to be analyzed is a non-homogeneous semi-solid product such as cottage cheese, meat, canned pet foods, etc., it can first be prepared for the fat extraction step by homogenizing the product in a blender with a mixture of methanol and aqueous citric acid or other suitable homogenizing agents known to the art. A volume of tetrachloroethylene, e.g. about 20 ml, is dispensed into the extraction tube and weighed to give a first weight ($W_1$). Some methanol, e.g. about 5 grams, then can be added without careful weighing. A given portion of the initially prepared (e.g., prepared by grinding) material is weighed (e.g., 0.5 grams to about 10 grams of the sample) to give a second weight ($W_2$) either directly in an extraction tube if more than about 2 grams, or separately in a weighing vessel if less than say about 2 grams. It is then most preferably quantitatively transferred into the extraction tube. After extraction, water also can be added to promote separation of the methanol and split the solvent into two phases. For certain aqueous liquids (and homogenates) only the methanol may be needed because sufficient water is already present. The mixture is then oscillated, preferably at about 3450 rpm, for about two minutes or as needed for complete extraction of the sample's fat content.

A few milliliters of the lower heavy solvent-extract phase is then aspirated from the extraction tube with a long cannula attached to a syringe pipet or other convenient means. A pressure-filter accessory can replace the cannula and the extract is then filtered into a suitable vial. A portion of the filtered extract is then fixed with a quantity of acetic acid. A small volume of an aqueous isopropanol surfactant solution is then uniformly mixed in with the filtered extract/acetic acid mixture in order to promote formation of fat globules in the liquid solution mixture.

The resulting turbidity in the liquid solution is caused by the scattered light from the generated fat globules. The maximum turbidity is best measured in a digital colorimeter, in its absorbance mode. Since the turbidity is not very sensitive to wavelength, any wavelength between about 450 nm and about 600 nm is usually satisfactory. A wavelength of about 480 nm is however somewhat preferred. Again, turbidity increases as more and more globules form. Simultaneously, some of the globules begin to coalesce which in turn causes less light to be scattered. These two opposing processes continue for several seconds until a maximum turbidity is attained. This maximum value is most conveniently measured as absorbance with the digital colorimeter. It is a nearly exact expression of the fat or oil concentration in the original tetrachloroethylene extraction, and indirectly, of the fat or oil concentration in the original food sample. In one highly preferred embodiment of this invention, the fat content of the original food sample is calculated by use of the equation: Percentage Fat (or Oil)=$C \times W_1/10 \times W_2$ where C is the milligrams of fat or oil per gram of tetrachloroethylene, $W_2$ is the weight in grams of sample subjected to extraction by the tetrachloroethylene, and $W_1$ is the weight in grams of tetrachloroethylene used. From the equation, % fat =$C \times W_1/10 \times W_2$ where C is mg fat per g of perchlor, $W_1$ is the grams of perchlor and $W_2$ is the grams of sample, one can insert nominal values for C and $W_1$ in order to calculate $W_2$ for a given expected percent fat. For example, $20=4 \times 32/10 \times W_2$. This tells us that the optimum sample weight should be about 0.640 grams. Hence, if one varies the perchlor by 3 grams, the sample weight will vary from 0.580 to 0.700 grams. Since the concentration can vary by 2 mg fat per gram of perchlor and still be on the standard curve, it is evident that the sample weight could be as small as 0.290 grams or as large as 1.050 grams. This, of course, is all contingent upon how closely one has guessed the expected fat content. If an estimation error is made, one simply starts over with a sample weight that will land us on the standard curve. A standard curve can be prepared, for example, by the method outlined below and then used to convert the measured maximum absorbance value of a sample being tested into a fat or oil concentration value.

To prepare a standard curve, the fat or oil in any given material is extracted by use of some official standard procedure and then used as a representative source for establishing a standard curve for that particular kind of material (cheese, milk, meat, oil bean, etc.). This curve is best established by measuring the maximum turbidities, of several exact concentrations of a given kind of fat or oil dissolved in tetrachloroethylene. The maximum absorbance values resulting from introduction of a surfactant and measurement of the resulting turbidity according to the processes of this patent disclosure are plotted against their respective concentrations.

It should be noted however that the turbidity measurements of both the tests to establish the reference curves and the tests to establish the fat concentration of a sample being tested are temperature dependent, and a systematic correction should be applied when measurements for the sample being tested are made at a temperature different from that of the prepared standard curve. For comparative uniformity, such standard curves are preferably measured at, or corrected to 23° C. Again, plots of some typical standard curves for the fat or oil extracted from several different materials (e.g., dairy fat and soybean oil) are shown in FIG. 1.

Because a given standard curve is preferably established by using the specific extracted fat or oil from the same kind of food product, this process is independent of other reference methods or calibrations. The food to be analyzed can also be a mixture of fat(s) or oil(s) from various sources. A given mixture of fat(s) and/or oil(s) is first extracted from the given mixture of foods and then a standard curve is established for that specific mixture of extracted fat(s) and/or oil(s).

Another general feature of this process is its ability to set or calibrate any digital colorimeter at a given value with an absorbance standard. By this procedure, the standard curve for a given fat or oil source, once established, can be used by any operator using a different digital colorimeter. Naturally, periodic verification of the digital colorimeter setting, along with any other needed adjustment is required.

One preferred protocol for carrying out the process of this patent disclosure is as follows:

APPARATUS AND REAGENTS

Use of an UDY Model OF Fat Analyzer including: Digital Colorimeter, Magnetic Stirrer, Bottle Top Dispensors, Dilutor Pipet, Extract-R-Reactor, and Pressure Filter along with Acetic Acid Reagent OF, Turbidity Reagent OFX and a Standard Calibration Sample Set are preferred. Also required and not included with the UDY Model OF are an Electronic Balance and possibly a Blender or Cyclone Sample Mill.

PROCEDURE

1. Grind 30 to 40 g of dry sample using screen. Blending with bentonite clay before grinding is useful for high fat or oil commodities. For meat products and other high moisture materials with over 8% fat content, prepare a 10-fold dilution by blending about 20 g of product with fixative diluent solution (one part methanol and two parts 2.0% citric acid). The amount of diluent to use is exactly nine times the actual weight of sample. The product is then blended until homogeneous (2 to 5 min.). If desired, the resulting product can be preserved with Udy-Pol for a shelf life of several weeks. For cheese or other similar products, reduction into pieces 3 mm or smaller is preferred. For samples under 8% fat, measure directly.

2. Add 20 ml of perchlor to the Extract-R-Tube; and record weight, $W_1$, in grams.

3. Now place enough ground, divided or dispersed sample (15 ml max.) into the Extract-R-Tube to give a concentration, C, of 3 to 5 mg fat per g of perchlor. This sample weight, $W_2$, in grams should be about 13 divided by the expected % fat. For liquid products, add about 5 g methanol. For non-liquid products, add about 5 g of methanol followed by about 5 g water, after extraction, to separate the methanol into an aqueous phase.

4. Extract for about 2 minutes at 3450 rpm or 4 minutes at 1725 rpm as necessary for complete extraction. When water is added, mix thoroughly, then after a well defined phase separation, use the syringe with cannula to aspirate about 6 or 7 ml from the lower solvent phase. Remove cannula. Then with the pressure filter assembly, filter extract through a 25 mm fiberglass filter disk into the 20 ml glass sample vial.

5. Set Digital Colorimeter absorbance at zero, using a well mixed blank solution of 5.00 ml acetic acid reagent OF, 3.50 ml Turbidity Reagent OFX, 0.350 ml perchlor and spinvane in a covered test tube cuvet. The blank must be clear.

6. Aspirate 0.350 ml of filtered extract with a dilutor pipet, then discharge this aliquot plus 5.0 ml of acetic acid into a clean dry disposable 16 mm test tube cuvet containing a magnetic spinvane. Discharge against the side of the tube to prevent splattering. This clear solution is stable for several hours.

7. While holding the tube in the fixture on top of the magnetic stirrer, position the dispensor pipet's delivery tip over the center of the tube.

8. Turn the stirrer on, then add 3.50 ml of turbidity reagent. After 6 to 7 seconds of mixing, turn the stirrer off.

9. Place this test tube cuvet in the digital colorimeter. Cover and read the highest absorbance value, A, as turbidity develops. Note room temperature and apply temperature correction of 0.007A per °C. Add when above, and subtract when below the calibration temperature (23° C.). For dairy products, the correction is 0.011A per ° C.

10. Prepare a standard curve for any given material using a standard calibration sample set. Temper and maintain all solutions within 0.5° C. Plot C vs. A adjusted to 23° C. Percent Oil or Fat=$CW_1/10W_2$.

The following example also serves to illustrate the application of this process (as well as a procedure for preparing a standard curve) to measurement of the fat content of different dairy products. First, a standard curve for dairy fat was established by extracting the fat from fresh butter according to the official AOAC method. Five exact concentrations of this pure fat, dissolved in tetrachloroethylene, were prepared at approximately 2, 3, 4, 5 and 6 mg of fat per gram of the tetrachloroethylene. Replicate maximum absorbance measurements (at least triplicate) were made for each concentration according to the process of this invention, and the average was plotted against its respective concentration. A smooth curve (such as the one shown for dairy fat in FIG. 1) joining these points can then serve as the standard curve for dairy fat.

Next, the maximum absorbance was measured according to the process of this invention for samples of cheese, ice cream and milk. The absorbance was converted to concentration by use of the prepared standard curve. Percent fat in each sample was calculated using the previously noted equation:

Percentage Fat=$C \times W_1/10 \times W_2$.

Comparison of the fat or oil percentage of various samples as obtained by the process of this invention and those of the official standard methods published in the "Official Methods of Analysis of the Association of Official Analytical Chemists", Fourteenth Edition 1984, also were made. The results are given in Table I below.

TABLE I

| Sample Source | % Fat or Oil | | Difference |
|---|---|---|---|
| | Std. Method | Equation (1) | |
| Chicken | 2.33 | 2.40 | +0.07 |
| Fish | 33.5 | 34.1 | +0.6 |
| Ground Beef | 19.2 | 18.8 | −0.4 |
| Lamb | 35.5 | 35.7 | +0.2 |
| Pork Sausage | 21.8 | 22.0 | +0.2 |
| Corn Meal | 3.12 | 3.09 | −0.03 |
| Peanut Butter | 54.9 | 54.5 | −0.4 |
| Soybean Meal | 18.0 | 18.1 | +0.1 |
| Sunflower Seed | 50.2 | 49.9 | −0.3 |
| Bovine Milk | 3.40 | 3.41 | +0.01 |
| Cheddar Cheese | 35.5 | 35.7 | +0.2 |
| Cheese Powder | 61.4 | 62.2 | +0.8 |
| Cottage Cheese | 2.35 | 2.38 | +0.03 |
| Cream | 28.6 | 29.0 | +0.4 |
| Cream Cheese | 33.6 | 34.0 | +0.4 |
| Evaporated Milk | 7.55 | 7.59 | +0.04 |
| Processed Cheese | 23.3 | 23.2 | −0.1 |

Those skilled in this art also will appreciate that while the above examples illustrate the application of this invention, the method is applicable to essentially all substances containing oils or fats. Slight variations in procedures may well present themselves to those skilled in this art without detracting from the scope and spirit of the invention described herein.

Thus having disclosed this invention, what is claimed is:

1. A process for determination of fat content of a fat-containing liquid food product, said process comprising:
   (1) mixing the fat-containing liquid food product with tetrachloroethylene and methanol in order to extract the liquid food product's fat content into the tetrachloroethylene and thereby form a fat extract-/tetrachloroethylene phase and an aqueous methanol phase which contains the remainder of the product;
   (2) filtering the fat extract/tetrachloroethylene phase and obtaining a measured portion of the filtered, fat extract/tetrachloroethylene phase;
   (3) mixing the measured portion of the filtered fat extract/tetrachloroethylene phase with a polar organic solvent selected from the group consisting of acetic acid, propionic acid, butyric acid, ethanol, propanol, and isopropanol in order to solubilize the fat content of the measured portion of fat extract-/tetrachloroethylene phase;
   (4) mixing the solubilized fat content of the measured portion of fat extract/tetrachloroethylene phase with an aqueous surfactant in order to transfer the solubilized fat content from the fat extract/tetrachloroethylene phase to the aqueous surfactant and thereby form colloidal globules of fat which are suspended in a resulting aqueous surfactant/fat suspension;
   (5) observing the resulting aqueous surfactant/fat suspension for a maximum in dispersion of monochromatic light;
   (6) comparing the maximum in dispersion of monochromatic light with a standard curve in order to determine the fat content of the liquid food product.

2. The process of claim 1 wherein the fat-containing liquid food product is milk.

3. The process of claim 1 wherein the fat-containing liquid food product is a meat homogenate.

4. The process of claim 1 wherein the polar organic solvent is acetic acid.

5. The process of claim 1 wherein the aqueous surfactant contains a nonionic, water soluble octylphenoxypolyethoxyethanol containing an average of 10 moles of ethylene oxide.

6. The process of claim 1 wherein the aqueous surfactant is a mixture of a nonionic, water soluble octylphenoxypolyehtyoxyethanol containing an average of 10 moles of ethylene oxide isopropanol and water.

7. The process of claim 1 wherein the observing of the aqueous surfactant/fat suspension for dispersion of monochromatic light is carried out by means of a digital turbidity detecting device.

8. The process of claim 1 wherein the observing of the solution for dispersion of monochromatic light is carried out by means of a spectrophotometer in its absorbance mode.

9. The process of claim 1 wherein about 32 parts by weight tetrachloroethylene and about 5 parts by weight methanol are used to extract the fat from the fat-containing liquid food product. The basis for this change can be found on page 27, lines 1-3.

10. The process of claim 1 wherein the determination of the fat content of the fat-containing liquid food product is made by use of the equation: Percentage fat = $C \times W_1 / 10 \times W_2$ where C is the milligrams of fat or oil per gram of tetrachloroethylene, $W_1$ is the weight in grams of the tetrachloroethylene used and $W_2$ is the weight in grams of the sample of fat-containing liquid food product subjected to extraction by the tetrachloroethylene.

11. A process for determination of fat content of a fat-containing solid food product, said process comprising:
  (1) reducing the fat-containing solid food product to a particle size which makes said solid food product susceptible to solubilizing;
  (2) dispersing the reduced solid food product in a solubilizing medium;
  (3) mixing the solid food product with tetrachloroethylene in order to extract the solid food product's fat content into the tetrachloroethylene and thereby form a fat extract/ tetrachloroethylene phase and another phase which contains the remainder of the said product;
  (4) filtering the fat extract/tetrachloroethylene phase and obtaining a measured portion of the filtered, fat extract/tetrachloroethylene phase;
  (5) mixing the measured portion of the filtered, fat extract/tetrachloroethylene phase with a polar organic solvent selected from the group consisting of acetic acid, propionic acid, butyric acid, ethanol, propanol, and isopropanol, in order to solubilize the fat content of the measured portion of fat extract/tetrachloroethylene phase;
  (6) mixing the solubilized fat content of the measured portion of fat extract/tetrachloroethylene phase with an aqueous surfactant in order to transfer the solubilized fat content from the fat extract/tetrachloroethylene phase to the aqueous surfactant and form colloidal globules of fat which are suspended in a resulting aqueous surfactant/fat suspension;
  (7) observing the resulting aqueous surfactant/fat suspension for a maximum in dispersion of monochromatic light;
  (8) comparing the maximum in dispersion of monochromatic light with a standard curve in order to determine the fat content of the solid food product.

12. The process of claim 11 wherein the solid product is an oil-containing seed.

13. The process of claim 11 wherein the polar organic solvent is acetic acid.

14. The process of claim 11 wherein the aqueous surfactant contains a nonionic, water soluble octylphenoxypolyethoxyethanol containing an average of 10 moles of ethylene oxide.

15. The process of claim 11 wherein the aqueous surfactant is a mixture of a nonionic, water soluble octylphenoxypolyethoxyethanol containing an average of 10 moles of ethylene oxide, isopropanol and water.

The basis for making these changes can be found on page 22, lines 16-18 of the patent application.

16. The process of claim 11 wherein the observing of the aqueous surfactant/fat suspension for dispersion of monochromatic light is carried out by means of a digital turbidity detecting device.

17. The process of claim 11 wherein the observing of the solution for dispersion of monochromatic light is carried out by means of a spectrophotometer in its absorbance mode.

18. The process of claim 11 where the solubilizing medium is water.

19. The process of claim 11 wherein tetrachloroethylene and methanol are used to extract the fat from the fat-containing solid food product.

20. The process of claim 11 wherein the determination of the fat content of the fat-containing solid food product is made by use of the equation: Percentage fat = $C \times W_1 / 10 \times W_2$ where C is the milligrams of fat or oil per gram of tetrachloroethylene, $W_1$ is the weight in grams of the tetrachloroethylene used and $W_2$ is the weight in grams of the sample of fat-containing solid food product subjected to extraction by the tetrachloroethylene.

* * * * *